United States Patent [19]

Wengrovius et al.

[11] Patent Number: 4,950,779

[45] Date of Patent: Aug. 21, 1990

[54] NONAQUEOUS METHOD FOR MAKING SILICONE OLIGOMERS

[75] Inventors: Jeffrey H. Wengrovius, Scotia; Virginia M. VanValkenburgh, Albany, both of N.Y.

[73] Assignee: General Electric Company, Schenectady, N.Y.

[21] Appl. No.: 445,249

[22] Filed: Dec. 4, 1989

[51] Int. Cl.[5] .............................................. C07F 7/08
[52] U.S. Cl. .................................... 556/457; 556/450; 556/455; 556/460
[58] Field of Search ........................ 556/457, 460, 450

[56] References Cited

U.S. PATENT DOCUMENTS

| 4,348,533 | 9/1982 | Alanko et al. | 556/457 |
| 4,382,145 | 5/1983 | Zeboah | 556/460 |
| 4,426,480 | 1/1984 | Petty | 556/457 X |
| 4,448,981 | 5/1984 | Tolenitino | 556/460 X |
| 4,539,232 | 9/1985 | Burzynski et al. | 556/457 X |

Primary Examiner—Paul F. Shaver
Attorney, Agent, or Firm—William A. Teoli; James C. Davis, Jr.; William H. Pittman

[57] ABSTRACT

A nonaqueous method is provided for making silicone oligomers by using stoichiometric amounts of formic acid to effect the condensation of polyalkoxysilanes or polyaminosilanes. Reaction can be effected under ambient conditions.

10 Claims, No Drawings

NONAQUEOUS METHOD FOR MAKING SILICONE OLIGOMERS

Background of the Invention

The present invention relates to a method for making silicone oligomers, such as cyclics, linear and branched organosiloxanes by effecting contact between an organosilane, such as a polyalkoxysilane, or polyaminosilane and formic acid under neat conditions.

Prior to the present invention, silicone oligomers such as linear polydiorganosiloxanes, or cyclic polydiorganosiloxanes were generally made by effecting hydrolysis of organohalosilanes, although aqueous condensation of alkoxysilanes, or aminosilanes are well known in the art. Gilman et al, JACS, 73 (1951), 968-970 report that a nonaqueous condensation of an alkoxysilane can be achieved with a silane, such as tris(pchlorophenyl)ethoxysilane using formic acid having about a, 90% by weight purity. It is also well known that nonhydrolytic condensation of an alkoxysilane can be achieved with some carboxylic acids or silylcarboxylates as reported by Noll, Chemistry and Technology of Silicones, Academic Press, 1968. However, optimal conditions for effecting nonhydrolytic condensation is not achieved unless a mineral acid is used in catalytic amounts at temperatures exceeding 100° C.

Summary of the Invention

It would be desirable to provide a method for making silicone oligomers, such as cyclics, linears and branched chain structures under nonaqueous conditions which did not require elevated temperatures. The present invention is based on the discovery that polyalkoxysilanes, or polyaminosilanes, can be converted under relatively mild conditions, such as at ambient temperatures, to silicone oligomers using stoichiometric amounts of formic acid. Surprisingly, acetic acid condensation of polymethoxysilanes has been found to require high temperatures, such as 100° C. along with a mineral acid catalyst to accelerate the reaction. On the other hand, it has been found that condensation of polymethoxysilanes with formic acid can proceed quickly under ambient conditions without a catalyst, under neat conditions.

Statement of the Invention

There is provided by the present invention a nonaqueous method for making silicone oligomers having from 3 to about 10,000 condensed siloxy units selected from cyclic, linear, branched and mixtures of such structures, which comprises (1) agitating at a temperature of from 20° C. to 150° C., substantially equal molar amounts of formic acid and an organosilane selected from the class consisting of polyalkoxysilanes and polyaminosilanes until the resulting mixture is substantially free of organosilane, and (2) recovering silicone oligomer from the mixture of (1).

Some of the polyalkoxysilanes which can be used in the practice of the present invention to make the silicone oligomers are for example, dimethyldimethoxysilane, methyltrimethoxysilane, dimethyldiethoxysilane, methyltriethoxysilane, vinyltrimethoxysilane, methylvinyldiethoxysilane, methylphenyldipropoxysilane, phenyltrimethoxylsilane, diphenyldimethoxysilane.

Some of the polyaminosilanes which can be used in the practice of the present invention to make the silicone oligomers are for example, $CH_3Si[N(C_2H_5)_2]_3$
$(CH_3)_2Si[N(C_2H_5)_2]_2$
$CH_3Si[N(CH_3)_2]_3$
$(CH_3)_2Si[N(CH_3)_2]_2$
$C_2H_3Si[N(C_2H_5)_2]_3$
$C_6H_5(C_2H_3)Si[N(C_2H_5)_2]_2$ In the practice of the present invention, reaction is preferably effected between equal molar amounts of formic acid with either polyalkoxysilane or polyaminosilane. However, in particular situations, from about 0.5 to about 1.25 mole of formic acid per mole of silane can be used without gellation occurring. It has been found that in certain instances, such as when a reaction is effected between formic acid and a particular polyalkoxysilane, such as a polymethoxysilane that an effective amount of an ion-exchange resin, for example, an acidic perfluorinated ion-exchange resin, such as Nafion ion exchange resin of E.I. Dupont de Nemours Co. can be added to the condensation mixture to accelerate reaction. An effective amount of ion-exchange resin is, for example, 0.001% to 5% by weight, based on the weight of reaction mixture.

It has been further found that condensation of an organoalkenyldialkoxysilane, such as methylvinyldiethoxysilane with formic acid, can favor the production of cyclic product. In instances where organotrialkoxysilane, such as methyltrimethoxysilane, or methyltriethoxysilane is condensed with formic acid, unique organotrisiloxy fluids containing cyclic, linear and branched species often result.

Recovery of the desired silicone oligomer from the condensation mixture can be achieved in most instances by a selective distillation procedure. For example, in instances where polyalkoxysilanes are condensed with formic acid, distillation of methylformate and methanol can be initially effected from the mixture, followed by the separation of various reaction components in order of their volatility.

In instances where the condensation is effected between the polyaminosilane and formic acid resulting in the production of formamide and condensed siloxane, a selective distillation of the resulting formamide and condensed siloxane has been found effective. In some instances, for example, the condensed siloxane can be initially separated, followed by the formamide, depending upon the relative volatility of the products of reaction.

The silicone oligomers made in accordance with the practice of the invention are free of mineral acid residues which can be detrimental in particular applications. Alkoxy end-capped or amine end-capped linear or cyclic products can be used as cross-linkers for RTV's or as coating for paper. These silicone polymers also can be used to impart scratch resistance to Lexan polycarbonate film surfaces.

The silicone oligomers made in accordance with the present invention also can be used in making room temperature vulcanizable compositions or as intermediates for making silicone block copolymers In addition, the method of the present invention facilitates regulation over the stoichiometry of the reactants providing greater control in predicting the molecular weight of the final product.

In order that those skilled in the art will be better able to practice the present invention the following examples are given by illustration and not by way of limitation. All parts are by weight unless otherwise indicated.

Example 1

A mixture of 5 grams (41.7mmol) of dimethyldimethoxysilane and 1.44 grams (31.3mmol) of formic acid were stirred together. A few crystals of Nafion perfluorinated ion-exchange powder was added to the mixture. The resulting mixture was stirred under nitrogen for 4 days. Based on GC analysis, there was obtained a quantitative yield of a linear polydimethylsiloxane having an average of 2 to 8 condensed dimethylsiloxy units and terminated with methoxy radicals. A trace amount of cyclic hexamethyltrisiloxane and octylmethyltetrasiloxane were also formed.

The above procedure was repeated except that 1.88 grams (31.3mmol) of acetic acid was substituted for the formic acid. It was found that little if any reaction occurred with the dimethyldimethoxysilane based on GC analysis.

Examole 2

A mixture of 10 grams (91 mmol) of methylvinyldiethoxysilane and 3.96 grams (86 mmol) of formic acid was heated under sealed conditions at 80° C. for 3 days. Volatiles were removed in vacuo and a colorless condensed silicone solution was recovered. Based on method of preparation, GC analysis, and $^1$HNMR and $^{29}$SiNMR analysis the product consisted of a major amount of a mixture of methylvinylcyclopolysiloxane having an average of 3 to 5 condensed units and a minor amount of a linear methylvinylsiloxane having an average of from 4 to 9 condensed methylvinylsiloxy groups and terminated with ethoxy radicals.

Example 3

Several mixtures were prepared of methyltrimethoxysilane with variable amounts of formic acid. For example, 5 grams (36.8mmol) of methyltrimethoxysilane was mixed separately with 1, 1.25, and 1.5 equivalents or 1.69 grams, 2.11 grams, and 2.54 grams of formic acid. A few crystals of Nafion perfluorinated ion-exchange resin also were added to each of the mixtures. The various mixtures were heated under sealed conditions at 80° C. for three days. It was found that the mixtures containing 1.5 and 1.25 equivalents of formic acid formed a gel with the methyltrimethoxysilane. However, the mixture containing only 1 equivalent of formic acid with methyltrimethoxysilane did not gel. A mixture of methyl formate and methanol were removed in vacuo from the ungelled mixture, resulting in a colorless solution. Based on GC-MS analysis and $^{29}$SiNMR analysis, it was found that the mixture contained cyclic methylmethoxysiloxane having an average of from 3 to 6 condensed methylmethoxysiloxy units. In addition the mixture contained branched and linear polymethylmethoxysiloxanes having terminal methoxy groups and an average of from 2 to 5 chemically combined methylmethoxysiloxy units. A similar result was obtained when methyltriethoxysilane was substituted for methyltrimethoxysilane.

It was further found that when one equivalent of trimethoxycyanoethylsilane was substituted for the methyltrimethoxysilane a colorless fluid resulted consisting essentially of condensed cyanoethylsiloxy units. The cyanoethylsiloxy fluid is found to impart improved resistance to the effects organic solvents when applied onto the surface of a paper substrate.

Example 4

There was added dropwise 4.5 grams (98.8mmol) of formic acid to 10 grams (49.4mmol) of bis(diethylamino)dimethylsilane. During the addition, an exothermic reaction resulted. Vacuum distillation of the resulting reaction mixture provided 9.5 grams of a mixture of octamethylcyclotetrasiloxane and hexamethylcyclopentasiloxane and diethylforamide. The resulting distillation residue was found to be an oil which contained higher molecular weight condensed silicones.

The silicone oil was applied onto the surface of a paper substrate. It was found that the resulting treated paper surface exhibited improved water resistance.

Example 5

A mixture of 500g of methyltrimethoxysilane, 126.8 grams of formic acid and 0.5g of Nafion perfluorinated ion exchange resin powder (10–35 mesh) were stirred together under nitrogen for 1 hour at 25° C. The mixture was heated to 90° C for two hours to effect the separation of methylformate and methanol as it formed. Volatiles were collected until the methyltrimethoxysilane had reacted. There was obtained 390g of product which was mainly linear polymethylmethoxysiloxanes having an $M_w$ of 1500.

The polymethylmethoxysiloxane is used to treat a Lexan polycarbonate film to improve its scratch resistance and solvent resistance.

Although the above examples are directed to only a few of the very many variables which can be used in the practice of the method of the present invention, it should be understood that a much broader variety of polyalkoxysilanes and polyaminosilanes can be used in combination with formic acid to provide a much broader variety of linear, cyclic and branched silicone oligomers.

What is claimed is:

1. A nonaqueous method for making silicone oligomers having from about 2 to about 10,000 condensed siloxy units selected from cyclic, linear, branched and mixtures of such structures, which comprises
    (1) agitating at a temperature of from 20° C. to 150° C., substantially equal molar amounts of formic acid and an organosilane selected from polyalkoxysilanes and polyaminosilanes until the resulting mixture is substantially free of organosilane, and
    (2) recovering the silicone oligomer from the mixture of (1).
2. A method in accordance with claim 1, where an ion-exchange resin is used to accelerate the reaction in (1).
3. A method in accordance with claim 1, where the organosilane is a polyalkoxysilane.
4. A method in accordance with claim 1, where the organosilane is a polyaminosilane.
5. A method in accordance with claim 1, where the polyalkoxysilane is dimethoxydimethylsilane.
6. A method in accordance with claim 1, where the polyalkoxysilane is an alkenylalkyldialkoxysilane.
7. A method in accordance with claim 1, where the polyalkoxysilane is methyltrimethoxysilane.
8. A method in accordance with claim 1, where the polyaminosilane is dimethylbis(diethylamino)silane.
9. A method in accordance with claim 1, where a mixture of alkylformate and alkanol is distilled from the mixture in step (1) as it forms.
10. A method in accordance with claim 9, where the alkyl formate is methylformate and alkanol is methanol.

* * * * *